United States Patent
Yoshida et al.

(10) Patent No.: US 7,381,435 B2
(45) Date of Patent: Jun. 3, 2008

(54) COMPOSITION FOR TREATING HEPATITIS C

(75) Inventors: Satoshi Yoshida, Tokyo (JP); Shuichi Kaneko, Kanazawa (JP)

(73) Assignee: Original Image Co., Ltd. (JP)

( * ) Notice: Subject to any disclaimer, the term of this patent is extended or adjusted under 35 U.S.C. 154(b) by 35 days.

(21) Appl. No.: 10/547,548

(22) PCT Filed: Mar. 4, 2004

(86) PCT No.: PCT/JP2004/002706

§ 371 (c)(1),
(2), (4) Date: Jun. 16, 2006

(87) PCT Pub. No.: WO2004/078191

PCT Pub. Date: Sep. 16, 2004

(65) Prior Publication Data

US 2007/0020348 A1    Jan. 25, 2007

(30) Foreign Application Priority Data

Mar. 5, 2003  (JP)  ............. 2003-059056

(51) Int. Cl.
*A61K 36/42*    (2006.01)
*A61K 36/286*    (2006.01)
*A61K 36/68*    (2006.01)
*A61K 36/355*    (2006.01)

(52) U.S. Cl. .............. 424/739; 424/758; 424/764; 424/738

(58) Field of Classification Search ............ None
See application file for complete search history.

(56) References Cited

U.S. PATENT DOCUMENTS

| | | | |
|---|---|---|---|
| 445,697 A | 2/1891 | Grout et al. | |
| 4,421,746 A | 12/1983 | Kojima et al. | |
| 4,456,597 A | 6/1984 | Kojima et al. | |
| 4,469,685 A | 9/1984 | Kojima et al. | |
| 5,837,257 A | * 11/1998 | Tsai et al. | .......... 424/741 |
| 5,882,672 A | * 3/1999 | Kojima et al. | .......... 424/438 |
| 5,929,038 A | 7/1999 | Chang | |

FOREIGN PATENT DOCUMENTS

| | | | |
|---|---|---|---|
| CN | 1077384 A | * | 10/1993 |
| CN | 1252292 A | * | 5/2000 |
| JP | 10-279491 | | 10/1998 |
| JP | 11-116498 | * | 4/1999 |
| JP | 2000-262226 | | 9/2000 |
| JP | 2000-281584 | | 10/2000 |

OTHER PUBLICATIONS

Hwang, Shinn-Jang, "Heapatitis C virus infection: an overview," Dec. 2001, J Microbiol Immunol Infect, 34(4): 227-234.*
Nishibe, et al., "Bioactive Components of Plantago Herb", Foods Food Ingredients J. Jpn., FFI Journal No. 166, pp. 43-49, (1995).
Chang, "Liver-Protective Activities of Aucubin Derived from Traditional Oriental Medicine", Research Communications in Molecular Pathology and Pharmocology, vol. 102, No. 2, pp. 189-204, (1998).
Imaoka, et al., "Chinese herbal medicines capable of IgE antibody suppression and IFN induction", J. Traditional Medicines, vol. 12, No. 3, 262(3.), pp. 257-263, (1995).
Seeff, et al., "Complementary and Alternative Medicine in Chronic Liver Disease", Hepatology, vol. 34, No. 3, pp. 595-603, (2001).
Hussein, et al., "Inhibitory Effects of Sudanese Medicinal Plant Extracts on Hepatitis C Virus (HCV) Protease", Phytotherapy Research, vol. 14, No. 7, pp. 510-516, (2000).
Kato, N., Hepatitis C Virus, Industrial Publishing & Consulting, Inc., Tokyo, 2000, pp. 167-182.
Kumagai, Naoki, Hepatitis C, Mainichi Life, Sep. 2002 issue, p. 23, The Yomiuri Shimbun, 2002.
Kato, N., Hepatitis C Virus, Industrial Publishing & Consulting, Inc., Tokyo, 2000, p. 188-201.
Hussein et al., Inhibitory Effects of Sudanese Medicinal Plant Extracts on Hepatitis C Virus (HCV) Protease, Phytotherapy Research (2000) 14, 510-516.
Lin et al., Medicinal Plants Used for the Treatment of Hepatitis in Taiwan, American Journal of Chinese Medicine, (1990) vol. XVIII. Nos. 1-2, pp. 35-43.
1995 report of the Anti-hepatitis A and B Study Group of the Ministry of Health and Welfare.
Sato et al., The N55A Region and the Prediction of Interferon Effect, in Progress of Medicinal Science, separate volume, "Search for the Onset and Progress Mechanism of Liver Disorders," issued on Feb. 5, 1999.
Yatsuhashi et al., HCV-RNA Levels and IFN Treatment, in Progress of Medicinal Science, separate volume, "Search for the Onset and Progress Mechanism of Liver Disorders," issued on Feb. 5, 1999.

(Continued)

*Primary Examiner*—Christopher R. Tate
*Assistant Examiner*—Heather L Anderson
(74) *Attorney, Agent, or Firm*—Finnegan, Henderson, Farabow, Garrett & Dunner, LLP

(57) ABSTRACT

By administering a composition comprising pumpkin seed, safflower, plantain and honeysuckle, subjective symptoms (for example, general malaise and abdominal swelling) of a patient with chronic hepatitis C can be eliminated and, moreover, objective symptoms diagnosed by a medical doctor (for example, liver enlargement and palm erythema) can be relieved or eliminated. From 1 to 3 months after the administration of the composition, a significant decrease in hepatitis C virus RNA level is gradually observed. Therefore, the above composition is useful at least as a composition for treating chronic hepatitis C. In particular, it is advantageous in treating a chronic hepatitis C patient showing a high chronic hepatitis C virus RNA level.

9 Claims, 1 Drawing Sheet

OTHER PUBLICATIONS

Oshita et al., Retreatment with Interferon in Patients with Hepatitis C, in Progress of Medicinal Science, separate volume, "Search for the Onset and Progress Mechanism of Liver Disorders," issued on Feb. 5, 1999.

Ikenoue et al., Interferon Therapy for Type C Chronic Hepatitis and Cirrhosis: Does Interferon Reduce the Incidence of Hepatocellular Carcinoma? in Progress of Medicinal Science, separate volume, "Search for the Onset and Progress Mechanism of Liver Disorders," issued on Feb. 5, 1999.

Suzuki et al., A Novel Interferon for the Treatment of Hepatitis C, Kan Tan Sui 43, (2), pp. 281-288, 2001.

* cited by examiner

COMPOSITION FOR TREATING HEPATITIS C

This application is the National Stage of International Application No. PCT/JP2004/002706, filed Mar. 4, 2004.

TECHNICAL FIELD

The present invention relates to a composition for the treatment of hepatitis C. In particular, the present invention relates to a composition for reducing the amount of chronic hepatitis C virus RNA, a composition for improving or reducing symptoms of chronic hepatitis C, a composition for suppressing cirrhosis progress in chronic hepatitis C, and a method for manufacturing these compositions.

BACKGROUND ART

Hepatitis C virus (HCV RNA virus) is the cause of hepatitis C. Infection occurs from body fluids such as the blood.

Hepatitis C virus (HCV) is classified into several subtypes according to the genetic type. There is a classification system which classifies HCV into types 1-6 and subtypes a, b, and c, which can be written as 1a, 1b, 2a, 2b, 3a, 3b, and so on (for example, Kato N., Hepatitis C Virus, Industrial Publishing & Consulting, Inc., Tokyo, 2000, p 168).

Sixty percents of people infected with HCV develop acute hepatitis after going through a 1-2 month incubation period. However, those infected with hepatitis C exhibit hepatic damage and slight symptoms, wherein the acute hepatitis period is not very clear. Acute hepatitis C advances to chronic hepatitis at a high rate (60-70%). Chronic hepatitis C causes abnormal AST (aspartate aminotransferase (also known as GOT, glutamate oxaloacetate transaminase)) and ALT (alanine aminotransferase (also known as GPT, glutamate pyruvate transaminase)) values. However, after 2-3 years, these values return to normal or close thereto. Since this state continues from several years to 10 years, doctors sometimes diagnose patients with chronic hepatitis C more than 10 years after the patient was infected with HCV. After repeated chronic necrotic and inflammatory reactions of the liver cells over a period of 20-30 years, hepatitis is known to progress into cirrhosis, and after a further 10 years, the cirrhosis progresses into liver cancer (Kumagai Naoki., Hepatitis C, Mainichi Life, September 2002 issue, p 23, The Yomiuri Shimbun, 2002).

In chronic hepatitis C patients, subjective symptoms are only recognizable during the active period. Symptoms include general malaise, malaise, poor appetite, nausea, and vomiting. If the disease continues to progress into cirrhosis, the percentage of patients exhibiting subjective symptoms rises to 80%. These patients exhibit additional symptoms such as a bloating sensation and skin pruritus. These patients may also exhibit symptoms such as abdominal pain, hematemesis, and melena. Major objective symptom is hepatic enlargement, and the incidence is estimated to be 60 percents. Other objective symptoms include enlargement of the left hepatic lobe, splenomegaly, swelling, ascites, erythema palmare, jaundice, and the like (Kato N., Hepatitis C Virus, Industrial Publishing & Consulting, Inc., Tokyo, 2000, p 189).

As a general therapeutic strategy for treating hepatitis C, the function of the liver is normalized and hepatitis is calmed for suppression of a disease progression. Based on the idea that the disease progression is suppressed by the calming of hepatitis while the virus exists in the body, a treatment comprising administering ursodeoxycholic acid (component comprising fel ursi), minor Bupleurum (Chinese herbal medicine comprising a decoction of seven crude drugs including Bupleurum root, *scutellaria*, pinellia tuber, (dried) fresh ginger, ginseng, jujube, and licorice), or a preparation comprising glycyrrhizinate of licorice as major constituents (strong neominophagen-C (SNMC®), in order to improve or reduce symptoms is widely known.

However, a more vigorously pursued method known as interferon (IFN) treatment for HCV viral clearance in the body in order to stop progress of the disease. In IFN treatment, two types of IFNs ($\alpha$ and $\beta$) are used for antiviral agents such as nIFN$\alpha$ (natural interferon $\alpha$), recombinant IFN$\alpha$ (genetic recombination-type interferon $\alpha$), nIFN$\beta$ (natural interferon $\beta$), and consensus IFN$\alpha$ [consensus interferon $\alpha$: interferon alphacon-1 (genetic recombination)]. There have been reported the complete responder from whom the virus is completely removed and the incomplete responder who is remarkably improving the hepatic functions by the use of IFN. IFN has also been acknowledged with the effect of suppression of the progress by decreasing the rate of the production of liver cancer.

In addition to IFN, lactoferrin can be given as a substance possessing an anti-virus effect on HCV. Lactoferrin is a glycoprotein belonging to the iron-binding trans-family having a molecular weight of about 80,000 and is obtained by binding a sugar chain of galactose or mannose to a polypeptide chain. The action mechanism of lactoferrin is believed to be the neutralization of the extracellular virus, thereby preventing infection.

It has been disclosed that when one or more of *Cucurbita moschata*, *Plantago asiatica*, and *Lonicera japonica* are added to feed, diseases, especially natural infections, caused by parasites, bacteria, and viruses are largely prevented, an enhancement of the biophylaxis, and an improvement of the quality of meets or eggs. Furthermore, it has been disclosed that a feed comprising crude drugs of *Cucurbita moschata*, *Plantago asiatica*, *Lonicera japonica*, and *Carthamus tinctorius* improves the health conditions, survival rates, quality of egg, and has anti-leucocytozoonosis effect in layers, and has an anti-Newcastle disease effect and inhibitory effects of the decreased number of Coccidium and Staphylococci in the intestine of quails (U.S. Pat. No. 5,882,672).

A method for producing an interferon inducer from the plants of the genus Cucurbitaceae such as pumpkin has been disclosed (U.S. Pat. No. 4,421,746). It has been disclosed that a methanol extract of winter squash (Sudan medicinal plant) exhibits an HCV protease inhibitory effect and that the inhibitory activity is 47.4±0.0% (Phytochemistry Research (2000) 14, 510-516). However, in this document, there is neither disclosed nor suggested about the decrease in hepatitis C virus under in vivo study. Also, it has been disclosed that *Plantago asiatica* (*Plantago* major L.) is used in the treatment of hepatitis virus (American Journal of Chinese Medicine, (1990) Vol. XVIII, Nos. 1-2, pp 35-43). However, this document reported that the treatment can be used for hepatitis which did not know exactly as hepatitis C, but did not mention or indicate that the treatment is actually effective. The antiviral activity and anti-tumor activity of interferon inducers extracted from the flowers of *Carthamus tinctorius* has been disclosed (for example, U.S. Pat. No. 4,456,597). It has also been disclosed that interferon inducers may be extracted from the flowers of *Lonicera japonica*, seeds of *Plantago asiatica*, and the like, and that the extracted interferon inducers are useful for the preventive and curative treatments of viral infections in humans and animals (U.S. Pat. No. 4,469,685). A macrophage activator comprising two crude drugs of *Cucurbita moschata* and *Carthamus tinctorius* has also been disclosed (JP-A-11-116498). A neutrophil activator comprising four crude drugs of *Cucurbita moschata, Carthamus tinctorius, Plantago asiatica*, and *Lonicera japonica* has also been disclosed (JP-A-2000-281584). However, while these documents disclose the interferon inducing effects, macrophage activating effects, neutrophil activating effects, and the inhibitory action of IgE anti-body production of the crude drugs used as active components in the present invention, none of the references disclose or suggest the hepatitis C antivirus activity of these crude drugs.

The progress of a curing method for "refractory chronic hepatitis C" which corresponds to the case that the patient carries a large amount of the virus in the blood (generally 100 KIU/ml or more) in particular among the chronic hepatitis C, type 1b has been desired (Kumagai Naoki, Hepatitis C, Mainichi Life, September issue, The Yomiuri Shimbun, Tokyo, 2002). Even when using interferon alpha-con-1, which has been introduced into the market as a hepatitis C curing agent with the highest complete recovery rate, it is reported that a complete recovery can not be expected if the amount of the virus is not less than 850 KIU/ml. It is known that the lower the amount of the virus, the better the recovery effect of the interferon treatment (1995 report of the Anti-hepatitis A and B Study Group of the Ministry of Health and Welfare, Progress of Medicinal Science, separate volume, "Search for the Onset and Progress Mechanism of Liver Disorders", issued on Feb. 5, 1999, Ishiyaku Publishers, Inc. Kan Tan Sui 43, (2), pp 281-288, 2001). Therefore, it is desirable for the amount of the virus to be as low as possible before starting the interferon treatment.

DISCLOSURE OF THE INVENTION

The present invention provides a composition for the treatment of chronic hepatitis C comprising *Cucurbita moschata, Carthamus tinctorius, Plantago asiatica*, and *Lonicera japonica* as active components, which can be combined with a conventional hepatitis C treatment, and is useful in the treatment of chronic hepatitis C which has conventionally been difficult to treat. More specifically, the present invention provides a composition for controlling the progress of chronic hepatitis C or improving the symptoms thereof and a method for producing the composition.

As a result of extensive studies on crude drugs obtained from plants, the present inventors have discovered that by administering a composition comprising *Cucurbita moschata, Carthamus tinctorius, Plantago asiatica*, and *Lonicera japonica* to chronic hepatitis C patients, particularly those carrying a large amount of chronic hepatitis C virus RNA in the blood, the composition has a surprising effect of improving subjective symptoms such as general malaise and a bloating sensation and objective symptoms diagnosed by a physician such as hepatic enlargement and erythema palmare, and that the hepatitis C virus RNA amount in the patients was gradually reduced when the composition was administered for a period of one month and three months. The present invention is based on this finding.

Specifically, aspects of the present invention relates to a composition for decreasing the amount of chronic hepatitis C virus RNA, comprising *Cucurbita moschata, Carthamus tinctoriuses, Plantago asiaticas*, and *Lonicera japonicas*; a composition for improving or relieving the symptoms of chronic hepatitis C, comprising *Cucurbita moschata, Carthamus tinctoriuses, Plantago asiaticas*, and *Lonicera japonicas*; and a composition for retarding the progress of chronic hepatitis C into cirrhosis, comprising *Cucurbita moschata, Carthamus tinctoriuses, Plantago asiaticas*, and *Lonicera japonicas*.

The present invention also provides a method for producing the above composition for lowering the amount of chronic hepatitis C virus RNA, the composition for improving or relieving the symptoms of chronic hepatitis C, and the composition for retarding the progress of cirrhosis resulting from chronic hepatitis C.

The present invention further provides an adjuvant composition for the treatment of chronic hepatitis C, which by combination with conventional treatments, preferably nIFNα, recombinant IFNα, consensus IFNα, peginterferon (PEG-IFN), IFNβ, IFN/ribavirin, and the like, strengthens the effect of interferon in the radical cure of chronic hepatitis C patients exhibiting a large amount of virus of 500 KIU/ml or more.

BEST MODE FOR CARRYING OUT THE INVENTION

Figure 1:
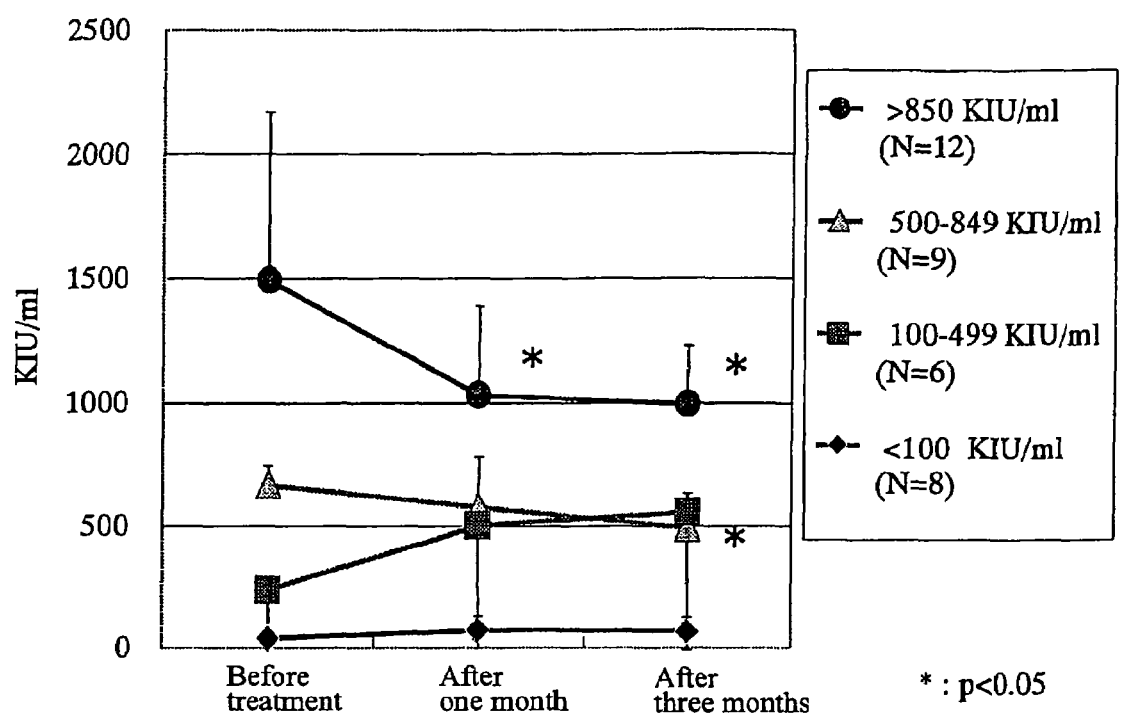
FIG. 1 is a graph showing the average quantity of HCV-RNA (KIU/ml) measured in Example 2.

The present invention will now be described in more detail.

First, the crude drug used in the present invention will be described.

*Cucurbita moschata* is the seed originates from a plant belonging to the genus *Cucurbitaceae* (known as pumpkin; *Cucurbita moschata* Duch.). In addition to these seeds, seeds of related plants capable of achieving the object of the present invention may also be used. Although these seeds may be used in their raw state, dry seeds are preferred because of their superior storability when used as a medicine or health food. The seed hull only may also be used. *Cucurbita moschata* comprise cucurbitin, protein, vitamins A, B1, B2, and C, carotene, and the like.

*Carthamus tinctorius* is the dried tubular flower of a plant belonging to the genus *Compositae* (known as safflower flower; *Carthamus tinctorius* Linne.). *Carthamus tinctoriuscomprises* Carthamin, safflor yellow, lignan, and sterol.

*Plantago asiatica* belongs to the genus Plantaginacea (known as; Plantain; *Plantago asiatica* Linne.) and its matured seeds (psyllium) or the entire plant (*plantago*) may be used. *Plantago asiatica* L. comprises polysaccharides, plantenolic acid, succinic acid, adenine, aucubin, plantaginin, and vitamins A and B1.

*Lonicera japonica* belongs to the genus *Gramineae* (known as honeysuckle; *Lonicera japonica* Thumb.) and its flower, bud, leaf, stem, or the entire plant may be used. *Lonicera japonica* comprises wax like materials, inositol, tannin, saponin, and lonicerin.

In the present invention, a crude powder of these crude drugs or an extract of these crude drugs obtained using water or an organic solvent may be used. Specifically, the crude drugs are used in the form of a crude powder, solvent preparation, powder preparation, compression, infusion, or the like.

As the organic solvent, ethanol, acetone, and the like can be given. A mixture of these organic solvents with water or a mixture of two or more organic solvents may be used. The extract can be obtained by adding the solvent in an amount of several times the crude drug and extracting or infusing the mixture at room temperature or with heating. Each of the crude drugs may be extracted separately and then combined, or a mixture of the crude powders of several crude drugs prepared beforehand may be extracted. The crude powder of these crude drugs can be obtained by chopping or powdering the raw plant, the material obtained by drying in the shade, or the dried material.

The above crude powder or extract obtained by extraction with water or an organic solvent of the crude drug may be used as it is, or prepared into a medicine, health food, or functional food (supplement) using conventional methods.

For example, the medicine or functional food (supplement) may be provided in the form of tablets, powder, granules, capsules, pills, or syrup for oral administration by a conventional method of preparation. During preparation, fillers, binders, disintegrating agents, lubricants, buffering agents, sweeteners, stabilizers, and the like may be used when necessary. In addition, at least one inert diluent such as lactose, mannitol, glucose, hydroxypropyl cellulose, finely crystallized cellulose, starch, polyvinyl pyrrolidone, and magnesium metasilicate aluminate may be used. In addition to the inert diluents, the composition may contain additives, for example, lubricants such as magnesium stearate, starch, and talc, disintegrating agents such as calcium cellulose glycolate, stabilizers such as lactose, and solubilizer adjuvants such as glutamic acid and aspartic acid in accordance with conventional methods. When necessary, tablets or pills may be coated with a sugar or a film of a substance soluble in the stomach or intestines such as sucrose, gelatin, agar, pectin, hydroxypropyl cellulose, and hydroxypropyl methyl cellulose phthalate.

Other additives may be added to the composition of the present invention to the extent that the effect of the crude drug active component is not adversely affected. Such additives include caffeine, water soluble vitamins such as vitamin B1, vitamin B2, vitamin B6, vitamin B12, vitamin C, biotin, carnitine, pantothenic acid, nicotinic acid, and derivatives thereof, fat-soluble vitamins such as vitamin A, vitamin E, and derivatives thereof, amino acids such as taurine and arginine, oriental herbs such as licorice root, ginkgo, dandelion, chrysanthemum, ginseng, and cinnamon, western herbs such as *Serenoa repens, Hypericum perforatum*, Echinacea, aniseed, annual chamomile (chamomile), rosemary, mint, eucalyptus, lavender, rose, hibiscus, and aloe. In addition, in accordance with the method of use, other active components such as oligosaccharides, such as lactulose, or commercial lactic acid bacteria such as bifidus may also be used.

Liquid compositions for oral administration include pharmaceutically accepted emulsions, solutions, suspensions, syrups, and elixirs, and comprise a commonly used inert diluent such as purified water and ethanol. In addition to the inert diluent, the composition may also comprise a moisturizer, an adjuvant such as a suspending agent, sweeteners, flavorants, aromatics, and antiseptics.

In the case of a health food, the composition can be provided in the form of a beverage or a confection such as a jelly, biscuit, cookie, or candy.

The composition of the present invention comprises crude drugs of *Cucurbita moschata* and *Carthamus tinctorius* in addition to *Plantago asiatica*, and *Lonicera japonica* as active components. Preferably, the present invention comprises *Cucurbita moschata* in a range from 20-60% by weight, *Carthamus tinctorius* in a range from 10-40% by weight, and each of the other crude drugs in a range from 5-70% by weight.

The amount of the active components to be administered can be appropriately determined based on the age, sex, and the like of the patient. Usually, in the case of an adult weighing 60 kg, the crude drugs are administered orally in a combined amount of 0.5-5 g and preferably 1-3 g on a daily basis. These guidelines also apply to health foods, supplements, and the like.

The chronic hepatitis C treatment adjuvant of the present invention exhibits a synergistically supporting effect in the treatment of hepatitis C when combined with the above-mentioned conventional treatments interferon and ursodeoxycholic acid. When the composition of the present invention is combined with the above-mentioned conventional hepatitis C treatments as an adjuvant, there are no restrictions to the order in which the drugs are administered. The drugs can be administered at the same time, the conventional treatments can be administered after administering the composition of the present invention for several months, or the composition of the present invention can be administered as a supporting treatment after administering the conventional treatment for several months.

Also, the composition of the present invention not only can be used in improving and reducing symptoms of hepatitis C virus disease in humans, but can also be used as a health food for the treatment and improving and reducing symptoms of hepatitis virus in companion animals such as dogs and cats.

EXAMPLES

The present invention will now be described in detail by way of examples and test examples, which should not be construed as limiting the present invention.

Example 1

(1) Measurement of the Amount of Hepatitis C Virus RNA in Chronic Hepatitis C Patients 26 chronic hepatitis C patients (13 men and 13 women range in age from 28 to 80 (the average age was 59.0)) receiving conventional treatment that exhibited a high amount of RNA at initiation of the testing were tested. A commercial product of the composition of the present invention known as InterPunch® (manufactured by Sanwell Co., Ltd.) was administered to the subjects in an amount of two packages (1.5 g per package) daily for three months. Before administration, and one month and three months after administration, the subjective symptoms, objective symptoms, and general biochemical measurement of the patients were observed and the HCV-RNA amounts were measured.

(2) Test Results

Four of the six patients exhibiting the subjective symptom of general malaise and one patient exhibiting a bloating sensation ceased to exhibit the symptoms after administration of the drug for one month. Two of the 13 patients exhibiting the objective symptom of hepatic enlargement and one of the six patients exhibiting erythema palmare ceased to exhibit the symptoms after administration for one month. In addition, none of the patients exhibited worsened subjective symptoms or objective symptoms after administration. General clinical examinations (hematological tests (number of leukocytes, number of red blood cells, amount of hemoglobin, hematocrit value, number of blood platelets, and leukocyte fractionation)) and biochemical tests (total protein, albumin, A/G, total bilirubin, AST, ALT, ZTT, LDH, alkaline phosphatase, γ-GTP, total cholesterol, TG, urea nitrogen, creatinine, Na, K, and Cl) were conducted in accordance with, for example, Japanese Liver Institute: Chronic Hepatitis Consultation Manual (Igaku-Shoin Ltd., Tokyo, 2001, ISBN: 426011977X) to confirm that the symptoms did not exhibit a tendency for worsening. The patients were separated into two groups, those carrying an RNA amount of 500-849 KIU/ml before administration and those carrying an RNA amount of 850 KIU/ml or more before administration, and were examined to confirm that the average RNA value of 1,447.7 KIU/ml of the group carrying an RNA amount of 850 KIU/ml or more (13 cases) was effectively decreased to 993.6 KIU/ml (p=0.032) after one month of administration and to 961.8 KIU/ml (p=0.015) after three months of administration. The average RNA value of 649.4 KIU/ml of the group carrying an RNA amount of 500-849 KIU/ml (13 cases) was effectively decreased to 527.5 KIU/ml (p=0.108) after three months of administration.

(3) Discussion

Eliminating the general malaise symptom improves life vitality and eliminating the uncomfortable abdominal feeling resulting from the bloating sensation causes physiological and mental pressures to disappear, thereby improving the quality of life (hereinafter referred to as "QOL") of the chronic hepatitis C patients. Hepatic enlargement is the most observed objective symptom used in the determination of chronic hepatitis C by a physician (refer to The clinical care and passage of chronic hepatitis C, Medicina, 30(3), pp 474-477, 1993), and the disappearance of the hepatic enlargement in the above two cases is a very significant sign in the treatment of chronic hepatitis.

Reduction in the amount of HCV-RNA resulting from the composition of the present invention was also confirmed. In the above cases, no particular side effects were observed and the composition of the present invention was confirmed to be effective in increasing the treatment effect of interferon when administered before the interferon treatment, thereby indicating that the composition of the present invention is effective as an adjuvant in the treatment of chronic hepatitis C.

Example 2

(1) Subjects

An open label examination of 50 registered patients receiving treatment for chronic hepatitis C including the 26 patients of Example 1 (26 males and 24 females, aged 28-80, with an average age of 59.0±10.6 (SD)) was carried out. The allocation standard was determined by the physician in charge and consent was obtained from each patient. The subjects were separated into group 1 (40 subjects) and group 2 (9 subjects) according to the HCV serotype, with one subject unclassified. 24 of the subjects had a history of IFN treatment.

Four subjects were removed from the experiment because administration was not proper, four subjects were removed from the experiment due to missing data, three subjects were removed from the experiment because they were administered IFN within six months of the start of the experiment, two subjects quit the experiment of their own accord, one subject was removed from the experiment because he began IFN treatment during the experiment, and one subject was removed from the experiment due to a concurrent hepatic tumor recognized before the experiment, for a total of 15 subjects removed from the experiment. The remaining 35 subjects (17 men and 18 women, aged 28-80, with an average age of 60.5±10.4 (mean±SD)) were analyzed. The subjects were separated into group 1 (27 subjects) and group 2 (7 subjects) according to serotype, with one subject unclassified. Fifteen of the subjects had a history of IFN treatment.

Twenty two of the subjects used an adjuvant for liver treatment during the experiment. Thirteen of the subjects had used ursodeoxycholic acid prior to initiation of the experiment and five subjects began using ursodeoxycholic acid during the experiment. Two subjects were administered a combination of a glycyrrhizin preparation and ursodeoxycholic acid, and another subject was administered a combination of KANTEC® and PROHEPARUM®. One subject was administered a combination of TAURINE POWDER® and ursodeoxycholic acid. Each of the remaining three subjects was administered single doses of AMINOLEBAN®, minor Bupleurum, and PROHEPARUM®, respectively.

(2) Test Substances

InterPunch® (manufactured by Sanwell Co., Ltd., Tokyo, Japan) of Example 1 was used as the test substance. InterPunch® was administered to each subject at a dosage of two 1.5 g packages daily (containing 1 g of an extract of a dry powder of four kinds of plants).

(3) Items of Examination

The six subjective symptoms of nausea and vomiting, abdominal pains, bloating sensation, hematemesis and melena, skin pruritus, and general malaise, and the five objective symptoms of hepatic enlargement, edema, ascites, erythema palmare, and jaundice were evaluated. The subjective and objective symptoms were confirmed by the physician in charge by discussion and palpation when the patient visited the hospital and were recorded on the patient's clinical chart. The items of blood test were the number of leukocytes, number of red blood cells, amount of hemoglobin, hematocrit value, number of platelets, and the rate of leukocytes per 100 cells. The items of biochemical test were AST, ALT, ALP, γ-GTP, ZTT, LDH, UN, creatinine, Na, K, Cl, total bilirubin, total protein, albumin, total cholesterol, and TG. The items of urine test were albumin, sugar, and occult blood. The HCV-RNA quantity was measured using the Amplicor method. Since the upper measurement limit is commonly 850 KIU/ml, values greater than this limit were remeasured using the dilution method. These items were measured before initiation of the treatment, one month after initiation, and three months after initiation.

(4) Statistical Analysis

The change in the blood test results, biochemical test results, HCV-RNA quantity, and HCV antibody assays were analyzed by the Student's t-test. The effect of the combination of the treatments was judged using a $\chi^2$ test.

(5) Discussion (i) Subjective and Objective Symptoms

In regard to the subjective symptoms, the results show that: Six subjects exhibiting the subjective symptom of general malaise before treatment, four subjects (66.7%) showed improvement after treatment for one month and continued to show improvement after three months. Of the two subjects exhibiting a bloating sensation before treatment, one subject showed improvement after treatment for one month (50%) and both subjects showed improvement after treatment for three months (100%). Of the two subjects exhibiting nausea and vomiting before treatment, one subject showed improvement after treatment for three months (50%).

In regard to the objective symptoms, the results show that, sixteen subjects exhibiting hepatic enlargement confirmed by palpation by a physician, one subject showed improvement after treatment for one month (6.3%) and two subjects showed improvement after treatment for three months (12.5%). Although no improvement was shown in the other symptoms, the subjective and objective symptoms exhibited by the subjects before treatment did not worsen during treatment. These results are shown in the following Table 1.

(ii) Hematological Test, Biochemical Test, and Urinalysis

There were no changes in the items in the hematological test. The treatment did not show any effect on the analysis of percentage of leukocytes. The results of the hematological test are shown in the following Table 2.

The biochemical test shows that the amount of ZTT of 17.5±7.6 IU/l before treatment increased significantly to 18.4±7.8 IU/l after treatment for three months (p<0.05). Although the amount of Na of 141.5±2.2 mEq/l before treatment increased significantly to 142.7±20 mEq/l after treatment for one month (p<0.01), the difference disappeared after three months of treatment (141.1±2.2 mEq/l). The biochemical test did not show any other changes in the functions of the liver and kidneys. The results of the biochemical test are shown in the following Table 3.

Urinalysis did not show any particular changes.

(iii) HCV-RNA Quantitative Determination and HCV Antibody Assays

The HCV-RNA for all 35 subjects was quantitatively determined and the mean±SD before treatment was 734.4±716.1 KIU/ml, 605.1±471.1 KIU/ml after one month of treatment, and 578.7±437.9 KIU/ml after three months of treatment. Although this shows a decrease with the lapse of time, a significant statistical change in the percentage of decrease was not recognized. However, by analyzing the results for each of the four ranges of the virus amount of 100 KIU/ml or less, 100-499 KIU/ml, 500-849 KIU/ml, and 850 KIU/ml or more, it was confirmed that the group of subjects carrying 850 KIU/ml or more (n=12) of the virus displayed a significant decrease after one month and three months of treatment (P=0.044 and P=0.024, respectively) (shown in FIG. 1). The group of subjects carrying 500-849 KIU/ml (n=9) of the virus also displayed a significant decrease after three months of treatment (P=0.021). Furthermore, in the one subject that carried 1.4 KIU/ml of the virus before treatment, the amount of the virus after one month of treatment was less than the detection sensitivity of the test.

As a result of statistically analyzing the antibody assays using the mean value of 25 subjects, the amount was 66.44±7.78 HCV-Ab index before treatment, 67.17±7.00 HCV-Ab index after one month of treatment, and 66.83±8.23 HCV-Ab index after three months of treatment showing no significant change. Also, no significant change was shown when the antibody assays was analyzed for each of the four ranges of virus amounts in the manner described above.

Furthermore, no significant correlation was found between the decrease in the amount of HCV-RNA and the change in AST and ALT. No significant difference was found between the presence of a drug comprising ursodeoxycholic acid and the change in the amount of HCV-RNA. Also, no particular tendency was found between the improvement of the subjective and objective symptoms and the amount of the virus.

(iv) Adverse Effects

Although a 71 year old woman exhibited diarrhea after one month of treatment, the diarrhea disappeared without suspending the treatment. A 60 year old man exhibited a slight bloating sensation after three months of treatment. No further adverse effects were exhibited.

(v) Discussion

Changes worth mentioning noticed during the present experiment include, by analyzing the results for each of the four ranges of the virus amount of 100 KIU/ml or less, 100-499 KIU/ml, 500-849 KIU/ml, and 850 KIU/ml or more, it was confirmed that the subjects carrying 850 KIU/ml or more of the virus exhibited a significant decrease in the amount of the virus after one month and three months of treatment/(p<0.05) and the subjects carrying 500-849 KIU/ml of the virus exhibited a significant decrease in the amount of the virus after three months of treatment (p<0.05).

In the present experiment, the group of subjects carrying a small amount of the virus of 500 KIU/ml or less did not exhibit a significant decrease in the amount of the virus. For a disease such as chronic hepatitis C in which the probability of spontaneous recovery is rare (refer to The clinical care and passage of chronic hepatitis C, Medicina, 30(3), pp 474-477, 1993), it is surprising that the amount of the virus in one of the subjects decreased to below detection sensitivity after treatment with the composition of the present invention. This indicates that the composition of the present invention has an effect on patients carrying a small amount of the virus.

In the present experiment, the subjects exhibiting a decrease in the amount of HCV-RNA did not clearly exhibit a decrease in AST and ALT, indicating that there is no correlation between the decrease in the amount of the virus and the function indication of the liver. Although there are reports describing that a decrease in AST and ALT is significant in the prognosis of liver disease, it is not presently clear if a virus decrease is clinically useful. Since the remarkable effectiveness of IFN depends on the amount of the virus, the results indicate that if the composition of the present invention were used in combination with another drug comprising interferon, the combination would be effective in the treatment of chronic hepatitis C.

In the very few cases of subjective symptoms, four of the six subjects exhibiting general malaise, both of the subjects exhibiting a bloating sensation, and one of the two subjects exhibiting nausea and vomiting showed improvement after three months of treatment. Also, in the cases of objective symptoms, of the 16 subjects who exhibited hepatic enlargement confirmed by palpation, two of these subjects ceased to exhibit this symptom after three months of treatment. Of the subjects exhibiting subjective and objective symptoms before treatment, none showed worsened symptoms after treatment. We believe that the improvement shown by the subject exhibiting general malaise indicates that the composition of the present invention contributes to an increase in QOL.

Two cases of adverse effects were observed in the present experiment, wherein in one case a subject exhibited slight diarrhea after one month of treatment. However, the diarrhea ended during treatment and was only temporary. The diarrhea could have resulted due to the presence of bifidus in the health food used in the experiment. A 60 year old man exhibited a bloating sensation after three months of treatment, but only to a slight degree. None of the other subjects exhibited any adverse effects and none of the 50 subjects, including those removed from the experiment because of efficiency analysis, exhibited any serious adverse effects resulting from treatment using the composition of the present invention.

IFN, which is widely used in the treatment of hepatitis C, causes side effects such as an influenza-like fever, joint aches, muscular aches, baldness, depression, eye disorders, loss of appetite, and loss of weight. However, the treatment using the composition of the present invention did not result in any serious adverse effects and its use in the treatment of hepatitis C is highly anticipated.

Blood and biochemical tests show that ZTT significantly increased after three months. Although the ZTT value reflects immunoglobulin (IgG) and indicates the reaction of mesenchyme used in the observation of the progress of chronic hepatitis patients, it does not directly indicate disorders in the liver cells. On the other hand, the AST and ALT values, which are indicators of hepatopathy, did not increase, the change in the amount of the HCV antibody was not clear, and the change in albumin fractionation was also not clear. A general judgment based on these observations would indicate that the increase in the amount of ZTT is not considered suggestive of a significant effect on the patient's own self-immunity phenomenon or cirrhosis. Also, although the amount of Na significantly increased after treatment for one month ($P<0.01$), the change was within the standard value and after three months of treatment returned to the initial value existing before the treatment. Therefore, it is not believed to be a significant side effect.

These results show that by administering the composition of the present invention to chronic hepatitis C patients, even those carrying a large amount of the virus, the amount of the virus can be decreased as soon as one month after treatment and that in some cases, subjective symptoms such as general malaise and objective symptoms such as hepatic enlargement can be improved. The composition of the present invention when combined with other treatments displays a synergistic effect in the treatment of chronic hepatitis C without causing deterioration of components of the blood biochemistry and without causing serious adverse effects.

TABLE 1

Subjective symptoms and objective symptoms

|  | Symptom | At test initiation | Number of improved subjects after initiation (improvement rate) | |
|---|---|---|---|---|
|  |  |  | After one month | After three months |
| Subjective symptoms | Nausea/vomiting | 2 | 0 | 1 (50.0%) |
|  | Bloating sensation | 2 | 1 (50.0%) | 2 (100%) |
|  | Skin pruritus | 1 | 0 | 0 |
|  | General malaise | 6 | 4 (66.7%) | 4 (66.7%) |
| Clinical symptoms | Hepatic enlargement | 16 | 1 (6.3%) | 2 (12.5%) |
|  | Swelling | 2 | 0 | 0 |
|  | Ascites | 1 | 0 | 0 |
|  | Erythema palmare | 7 | 0 | 0 |

TABLE 2

The results of Blood test

|  | Before administration | After one month | After three months |
|---|---|---|---|
| Number of red blood cells ($\times 10^4/mm^3$) | 3.9 ± 1.2 | 3.9 ± 1.2 | 3.9 ± 1.2 |
| Amount of hemoglobin (g/dL) | 433 ± 53 | 431 ± 52 | 432 ± 50 |
| Hematocrit value (%) | 13.6 ± 1.7 | 13.4 ± 1.6 | 13.4 ± 1.6 |
| Number of leukocytes (/mm$^3$) | 40.0 ± 4.6 | 39.6 ± 4.3 | 39.9 ± 4.3 |
| Number of platelets ($\times 10^4/mm^3$) | 12.6 ± 5.1 | 12.5 ± 5.2 | 12.4 ± 5.1 |

Note:
The data shown is the mean ± SD (34 cases). There was no significant statistical difference in any item.

TABLE 3

Biochemical test results

|  | Number of subjects | Before treatment | After one month | After three months |
|---|---|---|---|---|
| GOT (IU/L) | 35 | 59.7 ± 29.2 | 61.1 ± 30.2 | 57.4 ± 28.5 |
| GPT (IU/L) | 35 | 70.6 ± 39.6 | 68.9 ± 37.9 | 66.4 ± 35.4 |
| ALP (IU/L) | 35 | 335.1 ± 162.0 | 341.4 ± 168.9 | 342.9 ± 170.7 |
| γ-GTP (IU/L) | 35 | 53.9 ± 53.8 | 52.7 ± 48.8 | 50.6 ± 35.8 |
| ZTT (IU/L) | 34 | 17.5 ± 7.6 | 17.6 ± 7.3 | 18.4 ± 7.8* |
| LDH (IU/L) | 35 | 199.4 ± 41.4 | 198.2 ± 35.4 | 193.8 ± 31.6 |
| Total bilirubin (mg/dL) | 35 | 0.8 ± 0.3 | 0.8 ± 0.3 | 0.8 ± 0.4 |
| Total protein (g/dL) | 35 | 7.4 ± 0.5 | 7.4 ± 0.4 | 7.3 ± 0.5 |
| Albumin (g/dL) | 34 | 4.3 ± 0.5 | 4.26 ± 0.45 | 4.3 ± 0.4 |
| UN (mg/dL) | 34 | 15.9 ± 4.6 | 16.7 ± 4.4 | 15.9 ± 4.1 |
| Creatinine (mg/dL) | 34 | 0.7 ± 0.2 | 0.7 ± 0.2 | 0.7 ± 0.2 |
| Na (mEq/L) | 34 | 141.5 ± 2.2 | 142.7 ± 20** | 141.1 ± 2.2 |
| K (mEq/L) | 34 | 4.1 ± 0.4 | 4.2 ± 0.4 | 4.2 ± 0.4 |
| Cl (mEq/L) | 34 | 105.2 ± 2.4 | 105.9 ± 2.3 | 104.6 ± 2.2 |
| Total cholesterol (mg/dL) | 33 | 174.5 ± 38.5 | 172.9 ± 34.0 | 170.0 ± 33.8 |
| TG (mg/dL) | 33 | 104.9 ± 50.3 | 96.1 ± 42.2 | 107.6 ± 62.3 |

Note:
*$p < 0.05$;
**$p < 0.01$ (compared with before treatment): Mean ± SD.

There was a statistical significant increase in the amount of ZTT in the data after three months of treatment over that of before treatment.

There was a statistical significant increase in the amount of sodium in the data after one month of treatment over that of before treatment.

Example 3

5.0 g of *Cucurbita moschata*, 3.0 g of *Carthamus tinctorius*, 1.0 g of *Plantago asiatica*, 3.0 g of *Lonicera japonica*, 67 g of lactose, and 16 g of starch were mixed thoroughly in a vertical type blender. The mixture was kneaded with a kneading solvent that had been prepared in advance by dissolving 2 g of hydroxypropyl cellulose and 5 g of capric acid triglyceride into 40 g of 85% ethanol solution. The kneaded mixture was granulated in a basket-type granulator (screen diameter of 1 mm). The granules which were passed through a 14 mesh sieve were dried to obtain column-shaped granules. The above components were thoroughly mixed with mannite; hydroxypropyl cellulose, magnesium metasilicate-aluminate, aspartame, and fragrance to obtain 12 packages of fine granules (refer to JP 2000-231584).

Compositions with various component ratios (wt %) can be prepared in the same manner as that of Example 4 below.

TABLE 4

Composition example

| Formulation example | Cucurbita moschata | Carthamus tinctorius | Plantago asiatica | Lonicera japonica |
|---|---|---|---|---|
| 1 | 80 | 5 | 10 | 5 |
| 2 | 75 | 5 | 13 | 7 |
| 3 | 70 | 10 | 10 | 10 |
| 4 | 65 | 10 | 10 | 15 |
| 5 | 60 | 20 | 10 | 10 |
| 6 | 50 | 20 | 15 | 15 |
| 7 | 50 | 10 | 25 | 15 |
| 8 | 45 | 20 | 30 | 5 |
| 9 | 42 | 25 | 8 | 25 |
| 10 | 40 | 30 | 20 | 10 |
| 11 | 30 | 5 | 30 | 35 |
| 12 | 25 | 10 | 40 | 25 |
| 13 | 25 | 15 | 38 | 22 |
| 14 | 25 | 25 | 25 | 25 |
| 15 | 25 | 25 | 5 | 45 |
| 16 | 20 | 40 | 20 | 20 |
| 17 | 20 | 10 | 60 | 10 |
| 18 | 10 | 10 | 70 | 10 |
| 19 | 10 | 10 | 40 | 40 |
| 20 | 10 | 10 | 10 | 70 |
| 21 | 5 | 80 | 5 | 10 |

Example 4

Preparation example of a commercial product of the composition of the present invention known as InterPunch® manufactured by Sanwell Co., Ltd.).

Crude powder of crude drugs of *Cucurbita moschata*, *Carthamus tinctorius*, *Plantago asiatica*, and *Lonicera japonica* was mixed and the resulting mixture was extracted with 10 times the amount of water at a temperature of 95±5° C. for 30 minutes. After filtration, the extract was concentrated, excipients such as reducing maltose, lactose, starch, and the like, and fragrance were added to the extract, and the mixture was granulated to produce fine granules.

TABLE 5

Analysis example of nutrition per two packages of InterPunch

| | |
|---|---|
| Calorie | 11.5 Kcal |
| Protein | 0.042 g |
| Fat | 0.003 g |
| Sugar | 2.823 g |
| Dietary fiber | 0.03 g |
| Sodium | 0.444 mg |
| Lactulose | 400 mg |
| *Cucurbita moschata* | } Mixed extract equivalent to 1000 mg of raw material |
| *Plantago asiatica* seeds | |
| *Carthamus tinctorius* flowers | |
| *Lonicera japonica* floweres | |
| Bifidus | 40 mg |

Example 5

Safety

Formulation A of Composition of the Present Invention:

Components (mixed ratio of dried powder): *Cucurbita moschata* (50%), *Carthamus tinctorius* (20%), *Plantago asiatica* (15%), and *Lonicera japonica* (15%).

This formulation was administered to seven healthy male adults twice on a daily basis for a period of two weeks (each dose comprised 1.0 g of the crude drug). Before administration and after one week and two weeks from initiation, blood was collected and general clinical tests (hematology examination (number of leukocytes, number of red blood cells, amount of hemoglobin, hematocrit value, MCV, MCH, MCHC, number of blood platelets, and leukocyte fractionation)) and blood biochemical tests (total protein, albumin, A/G, total bilirubin, MCV, MCH, MCHC, AST, ALT, alkaline phosphatase, γ-GTP, total cholesterol, neutral fat, urea nitrogen, and creatinine), immunobiological tests (nonspecific IgE, nonspecific IgG, and transferrin), questioning, phonacoscopic tests, and physical tests (temperature, pulse, and blood pressure) were conducted by physicians to investigate the safety of the prescription of the composition of the present invention A. Also, the cell function (monocyte (macrophage in the blood) phagocytic activity and neutrophil phagocytic activity, NK-cell activity) and cytokine (IL2, 4, 6, 8, 10, 12, IFN-β, and TNF-α) were measured to investigate the safety of the health food of the present invention.

The results show that during the two week period of test administration, no adverse effects in clinical laboratory test values such as subjective symptoms, objective symptoms, or immunobiological tests seemed to occur as a result of the administration of the health food of the present invention, thereby confirming the safety of the health food of the present invention. No significant changes in cell function and cytokine were observed. It was judged that no measurable change could be found in a healthy male at this amount and period of administration.

Example 6

Safety

A commercial product of the composition of the present invention known as InterPunch was administered to a healthy male for a period of eight years (31 years of age at initiation). For the first two years, the subject was administered a daily average dosage equivalent to 1 g of crude drug powder of formulation A. Thereafter, the subject was administered a health food comprising formulation A at a daily average dosage equivalent to 1 g of the raw powder. The results show that no negative effects to general blood properties or state of health were observed during the period of administration.

INDUSTRIAL APPLICABILITY

The present invention provides a composition comprising *Cucurbita moschata, Carthamus tinctorius, Plantago asiatica*, and *Lonicera japonica* effective in relieving subjective symptoms in hepatitis C patients such as general malaise and bloating sensation, and objective symptoms diagnosed by a physician, for example improving conditions such as hepatic enlargement to a normal state and curing conditions such as erythema palmare. The composition reduces the amount of hepatitis C virus RNA after administration for a period of one and three months and is useful as a composition for the treatment of chronic hepatitis C, and more particularly, when administered before interferon treatment the composition increases the effect of interferon treatment. Hepatic enlargement in chronic hepatitis C patients is one indication used by physicians in determining the progress of hepatitis. Improvement in hepatic enlargement is very significant in the treatment of chronic hepatitis C and indicates that the composition is useful in preventing the hepatitis C from developing into cirrhosis and also preventing the cirrhosis from developing into liver cancer.

The present invention is particularly effective in chronic hepatitis C patients carrying a large amount of hepatitis C virus RNA. In addition, the composition of the present invention is useful in reducing the amount of hepatitis C virus RNA and improving and reducing symptoms of chronic hepatitis C. The composition of the present invention can be taken for a long period of time without fear of side effects and can be used in combination with conventional chronic hepatitis C treatments.

The invention claimed is:

1. A method for lowering the amount of chronic hepatitis C virus RNA in a patient suffering from chronic hepatitis C and exhibiting a viral RNA load of 500 KIU/ml or more, comprising administering an effective amount of a composition comprising *Cucurbita moschata, Carthamus tinctorius, Plantago asiatica*, and *Lonicera japonica* to the patient.

2. The method of claim 1, wherein the method further comprises administering an interferon or ursodeoycholic acid to the patient.

3. A method for improving or relieving one or more symptoms of chronic hepatitis C in a patient suffering from chronic hepatitis C and exhibiting a viral RNA load of 500 KIU/ml or more, comprising administering an effective amount of a composition comprising *Cucurbita moschata, Carthamus tinctorius, Plantago asiatica*, and *Lonicera japonica* to the patient.

4. The method of claim 3, wherein the method further comprises administering an interferon or ursodeoycholic acid to the patient.

5. The method of claim 3, wherein the one or more symptoms is hepatic enlargement.

6. The method of claim 3, wherein the one or more symptoms is erythema palmare.

7. The method of claim 3, wherein the one or more symptoms is general malaise or bloating.

8. A method for suppressing the progress of chronic hepatitis C into cirrhosis in a patient suffering from chronic hepatitis C and exhibiting a viral RNA load of 500 KIU/ml or more, comprising administering an effective amount of a composition comprising *Cucurbita moschata, Carthamus tinctorius, Plantago asiatica*, and *Lonicera japonica* to the patient.

9. The method of claim 8, wherein the method further comprises administering an interferon or ursodeoycholic acid to the patient.

* * * * *